United States Patent
Khalil et al.

(10) Patent No.: US 6,526,298 B1
(45) Date of Patent: Feb. 25, 2003

(54) METHOD FOR THE NON-INVASIVE DETERMINATION OF ANALYTES IN A SELECTED VOLUME OF TISSUE

(75) Inventors: Omar S. Khalil, Libertyville; Shu-jen Yeh, Grayslake; Charles F. Hanna, Libertyville; Stanislaw Kantor, Buffalo Grove, all of IL (US)

(73) Assignee: Abbott Laboratories, Abbott Park, IL (US)

( * ) Notice: Subject to any disclaimer, the term of this patent is extended or adjusted under 35 U.S.C. 154(b) by 124 days.

(21) Appl. No.: 09/693,122

(22) Filed: Oct. 20, 2000

Related U.S. Application Data

(63) Continuation-in-part of application No. 09/419,461, filed on Oct. 15, 1999, and a continuation-in-part of application No. 09/080,470, filed on May 18, 1998.

(51) Int. Cl.[7] .................................................. A61B 5/00
(52) U.S. Cl. ....................................................... 600/310
(58) Field of Search ................................ 600/310, 316, 600/322, 331, 336, 473, 476; 250/252.1

(56) References Cited

U.S. PATENT DOCUMENTS

| | | | |
|---|---|---|---|
| 3,628,525 A | 12/1971 | Polanyi et al. | |
| 3,638,640 A | 2/1972 | Shaw | |
| 4,223,680 A | 9/1980 | Jobsis | |
| 4,259,963 A | 4/1981 | Huch | |
| 4,432,365 A | 2/1984 | Leist | |

(List continued on next page.)

FOREIGN PATENT DOCUMENTS

| | | |
|---|---|---|
| DE | 42 42 083 | 6/1994 |
| DE | 44 17 639 | 11/1995 |
| DE | 196 34 152 | 3/1998 |

(List continued on next page.)

OTHER PUBLICATIONS

Graaff, et al., "Reduced light–scattering properties for mixtures of spherical particles: a simple approximation derived from Mie calculations", *Applied Optics*, vol. 31, No. 10, Apr. 1, 1992, pp. 1370–1376.

(List continued on next page.)

*Primary Examiner*—Eric F. Winakur
(74) *Attorney, Agent, or Firm*—David L. Weinstein

(57) ABSTRACT

A method for the determination of concentrations of analytes, e.g., glucose, and other metabolites in human tissue, wherein the temperature of a defined cutaneous volume of tissue, e.g., human skin, is controlled. The method involves calculating the concentration of an analyte in the tissue by taking into consideration the values of optical parameters of a sample of tissue measured in the defined cutaneous volume of the tissue at various temperatures. The selection of the defined volume is a function of the sampling distance along the surface of the tissue, the wavelength of light used to illuminate the tissue, and the temperature in the defined volume of tissue, which is a function of the temperature at the surface of the tissue. In one embodiment of the method of this invention, an optical signal re-emitted from a defined cutaneous volume of the tissue is measured, as the temperature of this volume is maintained at a constant value. In another embodiment of the method of this invention, the temperature of the defined cutaneous volume of the tissue is varied within a defined physiological range to change the depth of penetration of light into the tissue, thereby achieving a depth profile for the optical signal. The method of this invention is useful for monitoring the concentrations of analytes in tissues, testing at the point of care, and screening for diseases, such as, for example, diabetes. The method of this invention utilizes changes in temperature and selection of wavelengths to define cutaneous volumes below the surface of the tissue, in which volumes the concentration of an analyte can be determined.

27 Claims, 6 Drawing Sheets

U.S. PATENT DOCUMENTS

| | | | |
|---|---|---|---|
| 4,655,225 A | 4/1987 | Dähne et al. | |
| 4,882,492 A | 11/1989 | Schlager | |
| 4,890,619 A | 1/1990 | Hatschek | |
| 4,926,867 A | 5/1990 | Kanda et al. | |
| 4,975,581 A | 12/1990 | Robinson et al. | |
| 5,007,423 A | 4/1991 | Branstetter et al. | |
| 5,057,695 A | 10/1991 | Hirao et al. | |
| 5,068,536 A | * 11/1991 | Rosenthal | 600/316 |
| 5,086,229 A | 2/1992 | Rosenthal et al. | |
| 5,115,133 A | 5/1992 | Knudson | |
| 5,122,974 A | 6/1992 | Chance | |
| 5,131,391 A | 7/1992 | Sakai et al. | |
| 5,148,082 A | 9/1992 | Itou et al. | |
| 5,187,672 A | 2/1993 | Chance et al. | |
| 5,209,231 A | 5/1993 | Cote et al. | |
| 5,218,207 A | 6/1993 | Rosenthal | |
| 5,237,178 A | 8/1993 | Rosenthal et al. | |
| 5,277,181 A | 1/1994 | Mendelson et al. | |
| 5,284,139 A | 2/1994 | Khalil et al. | |
| 5,297,548 A | 3/1994 | Pologe | |
| 5,313,941 A | 5/1994 | Braig et al. | |
| 5,321,265 A | 6/1994 | Block | |
| 5,324,979 A | 6/1994 | Rosenthal | |
| 5,337,745 A | 8/1994 | Benaron | |
| 5,348,002 A | 9/1994 | Caro | |
| 5,348,003 A | 9/1994 | Caro | |
| 5,361,758 A | 11/1994 | Hall et al. | |
| 5,362,966 A | 11/1994 | Rosenthal et al. | |
| 5,372,136 A | 12/1994 | Steuer et al. | |
| 5,379,764 A | 1/1995 | Barnes et al. | |
| 5,383,452 A | 1/1995 | Buchert | |
| 5,402,778 A | 4/1995 | Chance | |
| 5,452,716 A | 9/1995 | Clift | |
| 5,481,113 A | 1/1996 | Dou et al. | |
| 5,492,118 A | 2/1996 | Gratton et al. | |
| 5,492,769 A | 2/1996 | Pryor et al. | |
| 5,497,769 A | 3/1996 | Gratton et al. | |
| 5,499,627 A | 3/1996 | Steuer et al. | |
| 5,515,847 A | 5/1996 | Braig et al. | |
| 5,533,509 A | 7/1996 | Koashi et al. | |
| 5,551,422 A | 9/1996 | Simonsen et al. | |
| 5,553,615 A | 9/1996 | Carim et al. | |
| 5,553,616 A | 9/1996 | Ham et al. | |
| 5,596,987 A | 1/1997 | Chance | |
| 5,665,530 A | 9/1997 | Oyamada et al. | |
| 5,672,875 A | 9/1997 | Block et al. | |
| 5,676,143 A | 10/1997 | Simonsen et al. | |
| 5,692,503 A | 12/1997 | Kuenstner | |
| 5,720,284 A | 2/1998 | Aoyagi et al. | |
| 5,725,480 A | 3/1998 | Oosta et al. | |
| 5,755,226 A | 5/1998 | Carim et al. | |
| 5,770,454 A | 6/1998 | Essenpreis et al. | |
| 5,782,755 A | 7/1998 | Chance et al. | |
| 5,823,951 A | 10/1998 | Messerschmidt | |
| 5,830,133 A | * 11/1998 | Osten et al. | 600/322 |
| 5,873,821 A | 2/1999 | Chance et al. | |
| 5,935,062 A | 8/1999 | Messerschmidt et al. | |
| 6,016,435 A | 1/2000 | Maruo et al. | |

FOREIGN PATENT DOCUMENTS

| | | |
|---|---|---|
| EP | 0 472 216 | 2/1992 |
| EP | 0 810 429 | 12/1997 |
| WO | 92/10131 | 6/1992 |
| WO | 92/20273 | 11/1992 |
| WO | 93/07801 | 4/1993 |
| WO | 93/13706 | 7/1993 |
| WO | 94/02837 | 2/1994 |
| WO | 94/05984 | 3/1994 |
| WO | 94/13199 | 6/1994 |
| WO | 95/20757 | 8/1995 |
| WO | 98/03847 | 1/1998 |
| WO | B1 99/55222 | 4/1999 |
| WO | 99/39631 | 8/1999 |
| WO | 99/59464 | 11/1999 |

OTHER PUBLICATIONS

Bruulsema, et al., "Correlation between blood glucose concentration in diabetics and noninvasively measured tissue optical scattering coefficient", *Optics Letters*, vol. 22, No. 3, 1997, pp. 190–192.

Heinemann, et al., "Non–invasive continuous glucose monitoring in Type I diabetic patients with optical glucose sensors", *Diabetologia*, vol. 41, 1998, pp. 848–854.

Kienle, et al., "Spatially resolved absolute diffuse reflectance measurements for noninvasive determination of the optical scattering and absorption coefficients of biological tissue", *Applied Optics*, vol. 35, No. 13, pp. 2304–2314.

Marbach, et al., "Noninvasive Blood Glucose Assay by Near–Infrared Diffuse Reflectance Spectroscopy of the Human Inner Lip", *Applied Spectroscopy*, vol. 47, No. 7, 1993, pp. 875–881.

Qu, et al., "Monte Carlo Modeling Studies of the Effect of Physiological Factors and Other Analytes on the Determination of Glucose Concentration In Vivo by Near Infrared Optical Absorption and Scattering Measurements", *Journal of Biomedical Optics*, vol. 2, No. 3, 1997, pp. 319–325.

Quan, et al., "Glucose determination by a pulsed photoacoustic technique: an experimental study using a gelatin––based tissue phantom", *Phys. Med. Biol.*, vol. 38, 1993, pp. 1911–1922.

Robbins, et al., "The Endocrine Pancreas", *Pathologic Basis of Disease, $3^{rd}$ Edition*, W. B. Saunders Company, 1984, pp. 972–990.

Tooke, et al., "Skin Microvascular Blood Flow Control in Long Duration Diabetics With and Without Complications", *Diabetes Research*, No. 5, 1987, pp. 189–192.

Wilson, et al "Progress toward the Development of an Implantable Sensor for Glucose", *Clinical Chemistry*, vol. 38, No. 9, 1992, pp. 1613–1617.

Jobsis, "Noninvasive, Infrared Monitoring of Cerebral and Myocardial Oxygen Sufficiency and Circulatory Parameters", *Science*, vol. 198, 1977, pp. 1264–1267.

Gopinath, et al., "Near–infrared spectroscopic localization of intracranial hematomas", *Journal of Neurosurgery*, vol. 79, 1993, pp. 43–47.

Zhang, et al., "Investigation of Noninvasive in VivoBlood Hematocrit Measurement Using NIR Reflectance Spectroscopy and Partial Least–Squares Regression", *Applied Spectroscopy*, vol. 54, No. 2, 2000, pp. 294–299.

Lin, et al., "Dynamics of tissue optics during laser heating of turbid media", *Applied Optics*, vol. 35, No. 19, 1996, pp. 3413–3420.

Laufer, et al., "Effect of temperature on the optical properties of *ex vivo* human dermis and subdermis", *Phys. Med. Biol.*, vol. 43, 1998, pp. 2479–2489.

Bruulsema, et al., "Optical Properties of Phantoms and Tissue Measured *in vivo* from 0.9–1.3 μm using Spatially Resolved Diffuse Reflectance", *SPIE Proceedings*, vol. 2979, 1997, pp. 325–334.

T. Shiga, et al., "Study of an Algorithm Based on Model Experiments and Diffusion Theory for a Portable Tissue Oximeter", *Journal of Biomedical Optics*, vol. 2, No. 2, Apr. 1997, pp. 154–161.

Jacques, et al., "Monte Carlo Modeling of Light Transport in Tissues", *Optical–Thermal Response of Laser–Irradiated Tissue*, edited by A.J. Welch and M.J.C. van Gemert, Plenum Press, New York, 1995, pp. 73–100.

Wilson, "Measurement of Tissue Optical Properties: Methods and Theories", *Optical–Thermal Response of Laser–Irradiated Tissue*, edited by A.J. Welch and M.J.C. van Gemert, Plenum Press, New York, 1995, pp. 233–274.

Morris, et al., "Basic Examination of Blood", *Clinical Diagnosis and Management by Laboratory*, 1996, pp. 549–559.

Lin, et al., "Dynamics of tissue reflectance and transmittance during laser irradiation", *SPIE Proceedings*, vol. 2134A Laser–Tissue Interaction V, 1994, pp. 296–303.

Burmeister, et al., "Noninvasive Blood Glucose Measurements by Near–Infrared Transmission Spectroscopy Across Human Tongues", *Diabetes Technology & Therapeutics*, vol. 2, No. 1, 2000, pp. 5–16.

Clarke, et al., "Evaluating Clinical Accuracy of Systems for Self–Monitoring of Blood Glucose", *Diabetes Care*, vol. 10, No. 5, Sep.–Oct. 1987, pp. 622–628.

U.S. application Ser. No. 09/080,470, filed May 18, 1998.
U.S. application Ser. No. 09/198,094, filed Nov. 23, 1998.
U.S. application Ser. No. 09/366,084, filed Aug. 3, 1999.
U.S. application Ser. No. 09/419,461, filed Oct. 15, 1999.
U.S. application Ser. No. 09/566,415, filed May 8, 2000.

\* cited by examiner

METHOD FOR THE NON-INVASIVE DETERMINATION OF ANALYTES IN A SELECTED VOLUME OF TISSUE

This invention is a continuation-in-part of U.S. Ser. No. 09/080,470, filed May 18, 1998, and U.S. Ser. No. 09/419,461, filed Oct. 15, 1999.

BACKGROUND OF THE INVENTION

1. Field of the Invention

This invention relates to devices and methods for the non-invasive determination of concentrations of analytes in a human subject in vivo and to methods of improving calibration of these devices and methods.

2. Discussion of the Art

Non-invasive monitoring of concentrations of analytes in the human body by means of optical devices and optical methods is an important tool for clinical diagnosis. "Non-invasive" (alternatively referred to herein as "NI") monitoring techniques measure in vivo concentrations of analytes in the blood or in the tissue without the need for obtaining a blood sample from the human body. As used herein, a "non-invasive" technique is one that can be used without removing a sample from, or without inserting any instrumentation into, the human body. The ability to determine the concentration of an analyte, or a disease state, in a human subject without performing an invasive procedure, such as removing a sample of blood or a biopsy specimen, has several advantages. These advantages include ease in performing the test, reduced pain and discomfort to the patient, and decreased exposure to potential biohazards. These advantages tend to promote increased frequency of testing, accurate monitoring and control of a disease condition, and improved patient care. A well-known non-invasive optical technique is pulse oximetry. Oxygenation of blood in the tissue and cerebral oxygen saturation can be measured by this technique, and the measurements can be used for clinical applications. Non-invasive determination of the hemoglobin concentration and the hematocrit value have the potential to be applied for diagnosis of anemia in infants and mothers, for localizing tumors, and for diagnosis of hematoma and internal bleeding.

Non-invasive diagnosis and monitoring of diabetes may be the most important non-invasive diagnostic procedure. Diabetes mellitus is a chronic disorder of carbohydrate, fat, and protein metabolism characterized by an absolute or relative insulin deficiency, hyperglycemia, and glycosuria. At least two major variants of the disease have been identified. "Type I" accounts for about 10% of diabetics and is characterized by a severe insulin deficiency resulting from a loss of insulin-secreting beta cells in the pancreas. The remainder of diabetic patients suffer from "Type II", which is characterized by an impaired insulin response in the peripheral tissues (Robbins, S. L. et al., *Pathologic Basis of Disease*, $3^{rd}$ Edition, W. B. Saunders Company, Philadelphia, 1984, p. 972). If uncontrolled, diabetes can result in a variety of adverse clinical manifestations, including retinopathy, atherosclerosis, microangiopathy, nephropathy, and neuropathy. In its advanced stages, diabetes can cause blindness, coma, and ultimately death.

Tight control of blood glucose level in the "normal range", 60–120 mg/dL, is necessary for diabetics to avoid or reduce complications resulting from hypoglycemia and hyperglycemia. To achieve this level of control, diabetics should test their blood glucose level several times per day. Thus, there is a need for accurate and frequent, preferably continuous, glucose monitoring to reduce the effects of diabetes.

U.S. Pat. Nos. 5,086,229; 5,324,979; and 5,237,178 describe non-invasive methods for measuring blood glucose level involving radiation in the near infrared region of the electromagnetic spectrum (600 nm to 1200 nm). In these methods, a blood-containing body part (e.g., a finger) is illuminated by one or more light sources, and one or more detectors detect the light transmitted through the body part. A glucose level is derived from a comparison to reference spectra for glucose and background interferants.

U.S. Pat. Nos. 5,362,966; 5,237,178; 5,533,509; and 4,655,225 describe the use of radiation in the near infrared range of the electromagnetic spectrum, that is, from 1200 nm to about 3000, for the optical measurement of blood glucose level. The principles of operation are similar to those described for measurements employing radiation in the 600 nm to 1200 nm range, except that the light penetration depth in this wavelength range is less than that in the 600 nm to 1200 nm wavelength range. As a consequence, most optical measurements in this region of the electromagnetic spectrum use an arrangement based on reflectance measurement rather than transmittance measurement. U.S. Pat. Nos. 5,313,941; 5,115,133; 5,481,113; 5,452,716; 5,515,847; 5,348,003; and DE 4242083 describe optical measurements in the infrared region of the electromagnetic spectrum employing radiation in the range of from about 3000 nm to about 25000 nm.

These glucose determination methods of the prior art are silent as to the effect of temperature at the measurement site on the optical signal. They are also silent as to the effect of temperature on the propagation of light in tissue and to the effect of modulating the temperature between preset limits during the optical measurement. U.S. Pat. Nos. 3,628,525; 4,259,963; 4,432,365; 4,890,619; 4,926,867; 5,131,391; and European Patent Application EP 0472216 describe oximetry probes having heating elements designed to be placed against a body part. U.S. Pat. No. 5,148,082 describes a method for increasing the blood flow in a patient's tissue during a photoplethysmography measurement by heating the tissue with a semiconductor device mounted in a sensor.

Spatially resolved diffuse reflectance techniques have been described U.S. Pat. Nos. 5,551,422; 5,676,143; 5,492,118; 5,057,695, European Patent Application EP 0810429. In these techniques, light is introduced into a sample and the intensity of the light re-emitted from the sample is measured at several distances from the site at which light is introduced into the sample. U.S. Pat. Nos. 5,187,672; 5,122,974; 5,492,769 and 5,492,118 describe frequency-domain reflectance measurements, which use optical systems similar to those used for spatially resolved diffuse reflectance measurements, except that the light source and the detector are modulated at a high frequency.

A major assumption for using these techniques is that tissue can be represented as an infinite-homogeneous slab. These techniques ignore the nature of skin, which is a layered structure. Further, these techniques ignore the effect of the temperature of the skin on propagation of light in cutaneous layers. U.S. Pat. No. 5,551,422 describes a glucose sensor utilizing spatially resolved diffuse reflectance techniques, wherein the sensor is brought to a specified temperature, preferably somewhat above normal body-temperature, with a thermostatically controlled heating system.

The light penetration depth in tissue depends on wavelength of the illuminating light. Generally, light in the near infrared region of the electromagnetic spectrum penetrates deeper into the tissue at longer wavelengths within the therapeutic window (600 nm to 1300 nm). Temperature affects the light penetration depth in tissue. Light at a given wavelength will penetrate deeper into a tissue, such as skin, as temperature of the tissue is lowered.

When human skin is illuminated by light of a single wavelength and the temperature of the skin is uncontrolled, the light penetration depth will vary from person to person, depending on the temperature of the subject's skin. When the skin is illuminated at a plurality of wavelengths and the temperature of the skin is not controlled, there will be even greater variation in light penetration depth. The ultimate result will be an erroneous estimate of optical parameters, and consequently, an erroneous determination of the concentration of an analyte in vivo.

U.S. application Ser. No. 09/080,470, filed May 18, 1998, assigned to the assignee of this application, and WO 99/59464 describe a non-invasive glucose sensor employing a means for controlling the temperature of a sample. One purpose of controlling the temperature of the skin during the optical measurement is to minimize the effect of physiological variables.

Although a variety of detection techniques have been disclosed in the art, there is still no commercially available non-invasive device that provides measurements of the concentrations of analytes with an accuracy that is comparable to that of measurements made by current commercially available invasive methods. Non-invasive measurements obtained by methods of the prior art are based on the assumption that the tissue, e.g., skin, comprises a single uniform layer that has a single uniform temperature. As a result, current approaches to non-invasive metabolite testing, such as monitoring of blood glucose level, hemoglobin determination or hematocrit monitoring, have not achieved acceptable precision and accuracy.

Thus, there is a need for improved devices and methods for non-invasive testing and quantification of analytes in the human body. It is desired that these methods and devices not be adversely affected by variations in temperature of the skin and that they account for the effects of the various optical properties of skin and the effect of temperature on the optical properties of the various layers of the skin.

SUMMARY OF THE INVENTION

This invention provides a method for the determination of concentrations of analytes, e.g., glucose, and other metabolites in human tissue, wherein the temperature of a defined cutaneous volume of tissue, e.g., human skin, is controlled. The method involves calculating the concentration of an analyte in the tissue by taking into consideration the values of optical parameters of a sample of tissue measured in the defined cutaneous volume of the tissue at various temperatures. The selection of the defined volume is a function of the sampling distance along the surface of the tissue, the wavelength of light used to illuminate the tissue, and the temperature in the defined volume of tissue, which is a function of the temperature at the surface of the tissue.

In one embodiment of the method of this invention, an optical signal re-emitted from a defined cutaneous volume of the tissue is measured, as the temperature of this volume is maintained at a constant value. In another embodiment of the method of this invention, the temperature of the defined cutaneous volume of the tissue is varied within a defined physiological range to change the depth of penetration of light into the tissue, thereby achieving a depth profile for the optical signal.

The method of this invention is useful for monitoring the concentrations of analytes in tissues, testing at the point of care, and screening for diseases, such as, for example, diabetes. The method of this invention utilizes changes in temperature and selection of wavelengths to define cutaneous volumes below the surface of the tissue, in which volumes the concentration of an analyte can be determined.

In one aspect, this invention provides a method for establishing a calibration relationship to determine the concentration of an analyte or a disease state in a biological tissue. The method comprises the steps of:

(a) selecting a sampling area on the surface of a biological tissue;

(b) setting the temperature of the sampling area of the biological tissue to a first temperature;

(c) introducing light at a light introduction site, the light introduction site being within the sampling area and collecting light re-emitted at a light collection site, the light collection site being within the sampling area, the light introduction site and the light collection site being separated by a sampling distance, the introduced light being within a first wavelength range;

(d) performing at least one optical measurement at the sampling distance;

(e) setting the temperature of the sampling area of the biological tissue to a second temperature, the second temperature being different from the first temperature;

(f) repeating steps (c) and (d) at the second temperature, the introduced light at the second temperature being within a second wavelength range;

(g) determining the value of at least one optical parameter at the first temperature and at at least one wavelength within the first wavelength range and the value of the at least one optical parameter at the second temperature and at at least one wavelength within the second wavelength range; and (h) establishing a mathematical relationship that relates the value of the at least one optical parameter at the first temperature and at the at least one wavelength within the first wavelength range and the value of the at least one optical parameter at the second temperature and at the at least one wavelength within the second wavelength range with an independently measured concentration of the analyte or an independent measurement of the disease state.

The aforementioned calibration relationship can be used to determine the concentration of an analyte or a disease state by means of a subsequent determination of at least one optical parameter at at least one wavelength and at least one temperature. In a preferred embodiment of this invention, at least one parameter can be selected from the group consisting of reflectance of the tissue, attenuation coefficient of the tissue, absorption coefficient of the tissue, scattering coefficient of the tissue, and depth of penetration of light in the tissue.

The temperatures at which the surface of the skin is maintained lie within a physiological temperature range, namely, from about 10° C. to about 45° C. Preferably, temperatures are selected so as to assure comfort during the measurements. Accordingly, a preferred temperature range is from about 15° C. to about 42° C., and a more preferred temperature range is from about 20° C. to about 40° C.

The light used in the method of this invention can have wavelengths ranging from about 400 nm to about 2000 nm, preferably ranging from about 500 nm to about 1800 nm. It is possible to select a range of wavelengths that allows the use of one type of detector. Thus, a wavelength range of from about 400 nm to about 1100 nm can be used with an inexpensive silicon photodiode detector, and a wavelength range of from about 700 nm to about 1900 nm can be used with an Indium/gallium arsenide detector. Preferably, the light introduced into the biological tissue has at least four wavelengths, at least two of the wavelengths being from about 500 nm to about 800 nm, and at least two of the wavelengths being from about 800 nm to about 1100 nm. Hybrid detectors having wider wavelength ranges can be used to detect light having wavelengths in all or most of the visible and near infrared regions of the electromagnetic spectrum.

The optical measurements for the method of this invention can be performed at a single sampling distance and at a plurality of wavelengths. This sampling distance defines the average depth in the sample at which the majority of the re-emitted light is collected and detected. The selection of the wavelengths and temperature further define the cutaneous volume from which the majority of the re-emitted light signal is scattered.

The volume of tissue subjected to temperature control and optical examination ranges from about 0.1 cubic millimeter to about 10 cubic millimeters, preferably from about 0.2 cubic millimeter to about 5 cubic millimeters, more preferably from about 0.2 cubic millimeter to about 2 cubic millimeters.

The method of this invention provides several advantages over methods and apparatus of the prior art used for the non-invasive determination of glucose and other analytes in the human body. Performing the optical signal measured at a single sampling distance eliminates the need for a plurality of light collection sites, the use of multiple detectors or multiple fibers. A single sampling distance leads to simpler, more robust optical instruments that are easier to calibrate and to maintain.

The method of this invention does not rely on calculating optical parameters that depend on the diffusion theory approximation or Monte Carlo simulations. Thus the calibration parameters obtained are independent of the assumptions that are usually used when applying the diffusion theory approximation or the Monte Carlo simulations.

Further, the method of temperature modulation of this invention can be used with prior art spatially resolved diffuse reflectance measurements to improve the correlation parameters, such as the correlation coefficient and the standard error of calibration, in meal-tolerance test or glucose tolerance test calibration procedures.

The method of this invention overcomes the shortcomings of the spatially resolved diffuse reflectance methods of the prior art by:

a) using a small measurement volume, in order to detect signal from an average depth of 1 to 3 mm in the tissue, thus avoiding adipose tissue and deep tissue structures;

b) allowing the monitoring of different depth in tissue, within a maximum depth of 3 mm;

c) offering simplified instrumentation that does not require illumination or collection of light at a plurality of positions;

d) allowing control and modulation of temperature in the shallow depth in tissue from where the optical signal is collected.

The method of this invention offers a novel use of combining temperatures and wavelengths to define a specific volume in tissue from which the signal to be measured is re-emitted, thereby improving the precision of the measurement.

BRIEF DESCRIPTION OF THE DRAWINGS

In FIG. 2A, the sampling distance is 0.44 mm.

In FIG. 2B, the sampling distance is 0.92 mm.

In FIG. 2C, the sampling distance is 1.84 mm.

DETAILED DESCRIPTION OF THE INVENTION

Figure 1:
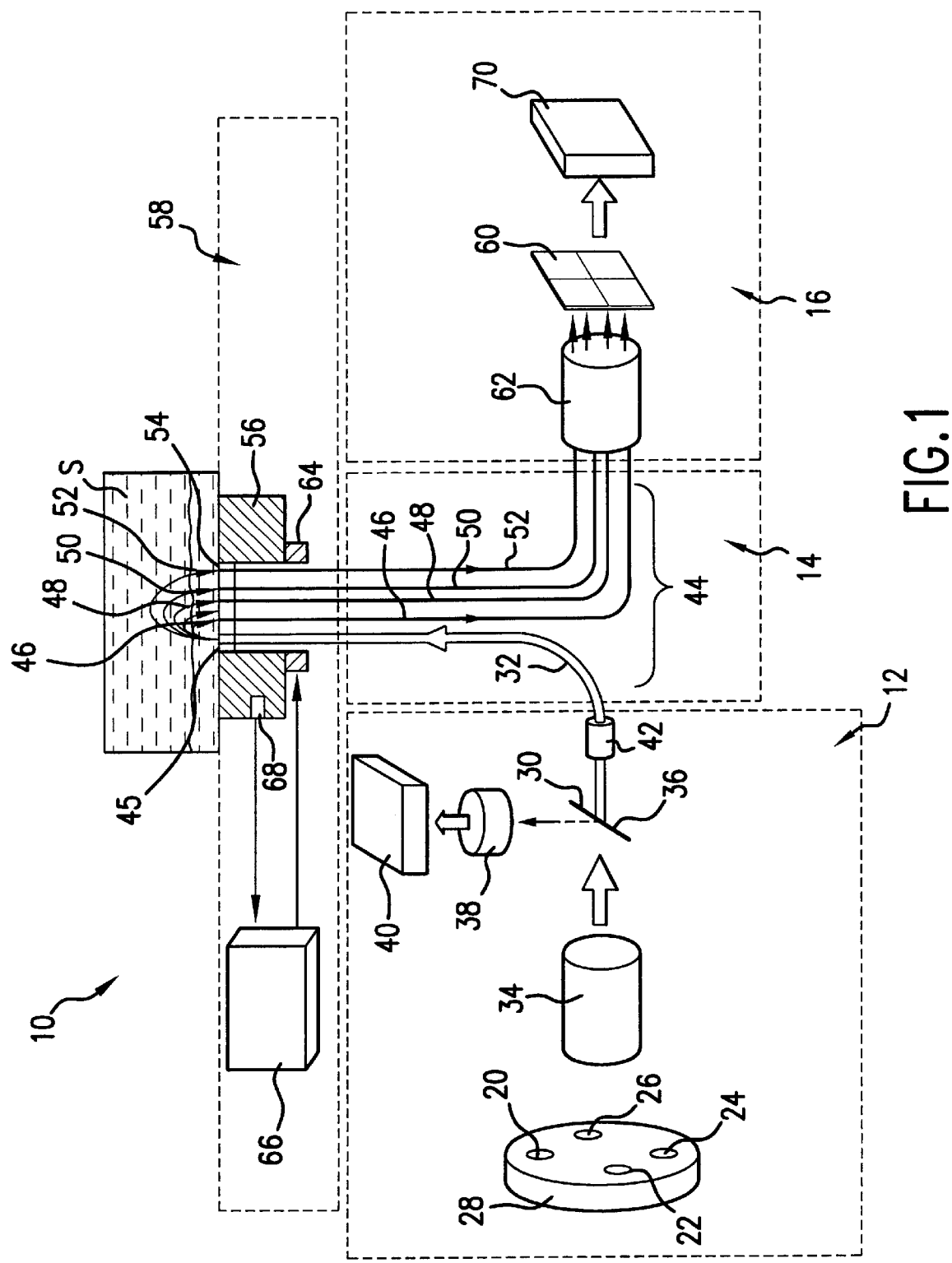
FIG. 1 is a schematic view of an optical system suitable for use in the method of this invention

As used herein, the expression "tissue optics" refers to the study of light propagation in biological tissues. The expression "optical property" refers to at least one of absorption, scattering, emission, reflectance, and depolarization property of biological tissues. The expression "optical parameter" refers to a parameter that describes and defines an optical property of a medium and its components. Examples of optical parameters include, but are not limited to, absorption coefficient, scattering coefficient, anisotropy factor, transport optical mean free path, and extinction coefficient of analytes. The expression "disease state" refers to a condition wherein a patient may have a disease that that be detected by the method of this invention. Such conditions include, but are not limited to, diabetes, a vascular disease, or a neoplastic disease, such as, for example, having a cancerous lesion.

The expression "scattering media" refers to media that both scatter light and absorb light. The expression "absorption coefficient" (i.e., $\mu_a$) refers to the probability of light absorption per unit path length, which is equal to 2.303 $\epsilon$C in cm$^{-1}$, where, $\epsilon$ is molar extinction coefficient and C is the molar concentration. The expression "scattering coefficient" (i.e., $\mu_s$) refers to the probability of light scattering per unit path length. The expression "anisotropy factor" (i.e., g) refers to the average cosine of the scattering angle for a multiply scattered photon. The expression "reduced scattering coefficient" (i.e., $\mu_s'$) refers to the probability of equivalently isotropic (uniform in all directions) scattering per unit path length, which is equal to $\sigma\rho$ in cm$^{-1}$, where, $\sigma$ is scattering cross section and $\rho$ is the number density of scattering centers. The reduced scattering coefficient is related to the scattering coefficient $\mu_s$ and the anisotropy factor g by the relationship $\mu_s'=(1-g)\mu_s$. Attenuation of light in turbid medium is described by the effective attenuation coefficient $\mu_{eff}=\sqrt{3\,\mu_{a(\mu_a+\mu_s')}}$.

The expressions "light penetration depth" and "depth of penetration of light" (i.e., $\delta$) refer to the rate of decay of intensity of light in scattering media with respect to the path traveled by the light in the same direction as the incident light. Light penetration depth represents the depth at which light intensity in the tissue is attenuated to 1/e of its original value. The effective attenuation coefficient $\mu_{eff}$ is the reciprocal of the light penetration depth $\delta$, i.e., $1/\mu_{eff}=1/\sqrt{(3\,\mu_{a(\mu_a+\mu_s')}}$. As described in U.S. Ser. No. 09/419,461, filed Oct. 15, 1999, a change in the temperature at the measurement site results in a change in light penetration depth in human skin; light penetration depth increases as the temperature is lowered below the body core temperature. The expression "change in light penetration depth as a function of temperature $\Delta\delta_T$" is defined as the difference in the value of the calculated light penetration depth in tissue at two preset temperatures, i.e. $\Delta\delta_T=\delta(T_1)-\delta(T_2)$. Alternatively, "change in light penetration depth as a function of temperature $\Delta\delta_T$" is defined as the product of the rate of change in light penetration depth as a function of temperature and the temperature interval in the measurement, i.e. $\Delta\delta_T(\partial\delta/\partial T) \cdot \Delta T$.

The expression "diffusion theory approximation" refers to an analytical solution describing the transport of light in tissue. The diffusion theory approximation assumes that the tissue is a semi-infinite slab of turbid medium. The approximation is valid where scattered light is collected far away from the source of light and the boundaries of the tissue, and the scattering coefficient is much larger than the absorption coefficient. The expression "Monte Carlo simulation" refers to a numerical method that can be used to statistically describe photon propagation in scattering media. The expression "diffuse reflectance" (reflectance therein unless specified otherwise) refers to measurement of light that is re-emitted from a sample at all angles different from the direction of the incident light, and over an area wider than the area where the incident light is introduced into the sample. The expressions "spatially resolved scattering" or "spatially resolved diffuse reflectance" and "localized reflection" refer to a measurement of light that is re-emitted from a sample and collected at several light collection sites at specific distances from a light introduction site. Alternatively, these expressions can refer to the light collected at a given light collection site on the sample boundary as a result of introducing light at discrete light introduction sites located on the same boundary at a set of defined distances from the light collection site. In both instances, $\mu_{eff}$, $\mu_a$ and $\mu_s'$ are calculated from the intensity distribution of the re-emitted light with respect to distances, i.e., the intensity of the re-emitted light at a multiplicity of sampling distances. The expressions "re-emitted light" and "reflected light" are used synonymously herein, as are the expressions "reflectance" and the "intensity of re-emitted light", unless otherwise indicated. The expression "frequency domain measurement" refers to a measurement of light involving the phase angle and/or the amplitude change of modulated incident light, at a given separation distance of a light introduction site from a light collection site, as the light transverses a scattering medium. The expression "beam of light" refers to a group of photons traveling together in nearly parallel trajectories toward a sample and striking the surface of the sample in a predefined area only. As a practical matter, the predefined area on the surface of a sample struck by a given beam of light is that area that is covered by an illuminating element, such as an optical fiber.

The expression "sampling area" means the area on the surface of a biological tissue wherein light is introduced and re-emitted light is collected and detected. The expression "biological tissue" refers to an intact human body part, human skin, excised human tissue, or animal tissue. The expression "optical measurement" refers to a physical measurement wherein light interacts with a sample of biological tissue and the transmitted, reflected, emitted, diffracted or scattered light is collected and detected.

The expression "light introduction site" means a location on the surface of a sample, e.g., a body part, tissue, or the like, at which light is injected or introduced into the sample.

The source of the light can be located at the light introduction site or can be located remote from the light introduction site. If the source of light is located remote from the light introduction site, the light must be transmitted to the light introduction site by light transmitting means, such as, for example, optical fibers. The expression "illuminating element" means a component located at the light introduction site that delivers light to the sample, e.g., a body part, tissue, or the like. The illuminating element is typically an optical fiber that transmits light from a source of light to the light introduction site. However, if the source of light is located at the light introduction site, the source of light can be the illuminating element. The expression "light collection site" means a location on the surface of a sample, e.g., a body part, tissue, or the like, at which light that is re-emitted from the sample is collected for measurement. The detector, which determines the intensity of the re-emitted light, can be located at the light collection site or can be located remote from the light collection site. If the detector is located remote from the light collection site, the light must be transmitted to the detector by light transmitting means, such as, for example, optical fibers. The expression "light collecting element" means a component located at the light collection site that collects light that is re-emitted from the sample, e.g., a body part, tissue, or the like. The light collecting element is typically an optical fiber that transmits light from the light collection site to a detector. However, if the detector can be located at the light collection site, the detector can be the light collecting element. The distance between a light introduction site and a light collection site, as measured along the surface of a sample, is defined as the "sampling distance". For a given sample, the sampling distance determines the mean distance from the surface of the sample into the interior of the sample at which the scattering and absorption events contribute to the measured re-emitted light. Such mean distance is hereinafter referred to as the "sampling depth", which is a function of the sampling distance. According to this invention changing the temperature of the tissue modifies the sampling depth in human skin; sampling depth increases as the temperature is lowered within the physiological temperature range of the body.

As used herein, the expression "physiological temperature range" of a biological sample means the temperature range over which the biological activity of the sample is maintained, without irreversible change in the its optical or biological properties as a result of changing temperature.

As used herein, the expression "Clarke error grid" refers to a data analysis and presentation tool that provides a quick estimation of the accuracy of a measurement relative to a reference method. Data obtained by means of a test device is plotted against data obtained by means of a reference method. A scatter diagram is prepared and divided into five zones, namely A, B, C, D, E zones. Data points falling in zone A represent acceptable performance while data points falling in zones C, D, and E represent unacceptable performance. A personal glucose monitor is deemed to provide acceptable performance if more than 95% of the data points of the scatter diagram are in the A zone, less than 5% of the data points are in the B zone. None of the data points should fall in the C, D, and E zones. This outcome will be approximately equivalent to a total error of 20% at blood glucose levels above 60 mg/dL. The performance of the test device is considered better if the percentage of data points falling in the A zone increases and the percentage of the data points falling in the B zone decreases. A constant error value (i.e., not a percentage) is used below a concentration of 60 mg/dL. Data points falling in the C, D and E zones represent progressively increasing deviation between the glucose monitor and the reference method. This increased inaccuracy may lead to the wrong type of intervention. As used herein, the term "calibrate" means establish a mathematical relationship between a measured optical signal and the concentration of an analyte determined by an independent method. The relationship is established by performing measurements on a number of samples designated as the calibration set. The term "prediction" refers to the ability to determine the concentration of an analyte in an unknown sample from a calibration relationship, wherein the sample is not one of those in the calibration set. Statistical performance parameters are the standard error of calibration, SEC, which tests the closeness of the fit between a measured signal by one detection method and the concentration of glucose determined by a reference method. The standard error of cross-validation prediction, CV-SEP, is an estimate of the prediction power of the calibration model. This measurement is obtained by taking one data point from the calibration data set, using it as an unknown, and rotating through all the data points in the set, one at a time. A better method for determining the ability of a calibration model to predict the concentration of glucose (alternately referred to herein as "blood glucose level") is the standard error of prediction, SEP, which represents the precision with which the calibration model can predict data points that are not part of the calibration data set.

In one aspect, this invention involves a method for establishing a calibration relationship to determine the concentration of an analyte or a disease state in a biological tissue. The method comprises the steps of:

(a) selecting a sampling area on the surface of a biological tissue;

(b) setting the temperature of the sampling area of the biological tissue to a first temperature;

(c) introducing light at a light introduction site, the light introduction site being within the sampling area and collecting light re-emitted at a light collection site, the light collection site being within the sampling area, the light introduction site and the light collection site being separated by a sampling distance, the introduced light being within a first wavelength range;

(d) performing at least one optical measurement at the sampling distance;

(e) setting the temperature of the sampling area of the biological tissue to a second temperature, the second temperature being different from the first temperature;

(f) repeating steps (c) and (d) at the second temperature, the introduced light at the second temperature being within a second wavelength range;

(g) determining the value of at least one optical parameter at the first temperature and at at least one wavelength within the first wavelength range and the value of the at least one optical parameter at the second temperature and at at least one wavelength within the second wavelength range; and (h) establishing a mathematical relationship that relates the value of the at least one optical parameter at the first temperature and at the at least one wavelength within the first wavelength range and the value of the at least one optical parameter at the second temperature and at the at least one wavelength within the second wavelength range with an independently measured concentration of the analyte or an independent measurement of the disease state.

The aforementioned calibration relationship can be used to determine the concentration of an analyte or a disease state by means of a subsequent determination of at least one optical parameter at at least one wavelength and at least one temperature. In a preferred embodiment of this invention, at least one parameter is selected from the group consisting of reflectance of the tissue, attenuation coefficient of the tissue, absorption coefficient of the tissue, scattering coefficient of the tissue, or depth of penetration of light in tissue.

The temperatures at which the area of the skin is maintained lies within the physiological temperature range, from about 10° C. to about 45° C. Because temperatures are preferably selected to assure comfort during the measurements, a preferred range is from about 15° C. to about 42° C., and a more preferred range is from about 20° C. to about 40° C.

The wavelength of light used in this invention ranges from 400 nm to 2000 nm, preferably from about 500 nm to about 1800 nm. The range between 400 and 1100 nm can be used with a silicon detector and a range between 700 and 1900 nm can be used with an Indium/gallium arsenide detector. Preferably, the light introduced into the tissue has at least four wavelengths, at least two of the wavelengths being from about 500 nm to about 800 nm, and at least two of the wavelengths being from about 800 nm to about 1100 nm. Hybrid detectors having wider wavelength ranges can be used to detect light having wavelengths in all or most of the visible and near infrared regions of the electromagnetic spectrum.

The volume of tissue subjected to temperature control and optical examination ranges from about 0.1 cubic millimeter to about 10 cubic millimeters, preferably from about 0.2 cubic millimeter to about 5 cubic millimeters, more preferably from about 0.2 cubic millimeter to about 2 cubic millimeters.

The effect of temperature variation on the scattering and absorption properties of tissue has been of interest in the art of non-invasive monitoring. Thermal effects of laser excitation, photocoagulation, and the effects of temperature on the optics o f the skin have been described in the art. See, for example, W-C. Lin et al., "Dynamics of tissue reflectance and transmittance during laser irradiation", SPIE Proceedings, 2134A Laser-Tissue Interaction V (1994) 296–303; and W-C. Lin, "Dynamics of tissue optics during laser heating of turbid media", Applied Optics (1996) Vol. 35, No. 19, 3413–3420. See also J. Laufer et al., "Effect of temperature on the optical properties of ex vivo human dermis and subdermis", Phys. Med. Biol. (1998) Volume 43, 2479–2489; and J. T. Bruulsema et al., "Optical Properties of Phantoms and Tissue Measured in vivo from 0.9–1.3 $\mu$m using Spatially Resolved Diffuse Reflectance", SPIE Proceedings 2979 (1997) 325–334.

In order to appreciate the effects of temperature variations on non-invasive measurements, it may be helpful to review the theoretical description of light propagation in tissues. A discussion of optical properties of tissue and the effect of these properties on light scattering and absorption is provided below. The dependence of non-invasive measurements on temperature of the tissue is also illustrated, and preferred embodiments for controlling the temperature of non-invasive measurements are described.

Light fluence within a turbid sample such as a sample of human tissue, where light may undergo scattering events, is described in the art by the following formula:

$$I = I_o \exp(-\mu_{eff} z) \qquad (1)$$

where $I_o$ represents the intensity of the incident light,

I represents the intensity of the light at a depth z from the surface of the sample, and $\mu_{eff}$ defined as:

$$\mu_{eff} = \sqrt{(3\mu_a[\mu_a + \mu_s(1-g)])} = \sqrt{(3\mu_a(\mu_a + \mu'_s))} \qquad (2)$$
$$= 1/\delta$$

where $\delta$ expresses the light penetration depth, $\delta$, which refers to the rate that intensity of light decays, as a function of distance, in turbid media along the direction of light introduction.

Light penetration depth $\delta$ is a statistical representation of the distance measured from the surface of the sample to the interior of the sample at which intensity of light is attenuated to 1/e of its incident value, where e is the base of the natural logarithm. The distance is measured along the direction of incident light. Light penetration depth corresponds to the depth in tissue, z, wherein 37% of the intensity of incident light is maintained. According to equation (1), $$I(\text{when } z=\delta)=I_o/e=0.371I_o \qquad (3)$$

Because the value of $\delta$ depends on both $\mu_a$ and $\mu'_s$, an increase in either of $\mu_a$ or $\mu'_s$ will lead to a decrease in the light penetration depth $\delta$ in the tissue. Conversely, a decrease in the value of either of these two coefficients will lead to an increase in the light penetration depth in the tissue.

U.S. Ser. No. 09/419,461, filed Oct. 15, 1999, incorporated herein by reference, describes a method for modulating depth of light penetration in tissue and discloses diagnostic applications employing the step of modulating the depth of light penetration. The effect of varying the temperature between two pre-set values (such as, for example, between 38° C. and 22° C.) on the optical parameters of human skin was described in U.S. Ser. No. 09/419,461, filed Oct. 15, 1999.

As described in U.S. Ser. No. 09/419,461, filed Oct. 15, 1999, a decrease in temperature results in a decrease in the scattering coefficient as well as the absorption coefficient of tissue. Changes in the absorption and scattering coefficients as a function of temperature will inversely affect light penetration depth in tissue because $\delta=1/\sqrt{3\mu_a(\mu_a+\mu_s)}$. Change in light penetration depth ($\delta$) can be achieved by two mechanisms that occur concurrently. First, a decrease in blood flow to the subsurface capillaries, i.e. a decrease in $\mu_a$ of the top layers, can lead to an increase in $\delta$. Secondly, a decrease in the scattering coefficient as temperature is lowered can also lead to an increase in $\delta$. An increase in light penetration depth allows the sampling of the larger blood vessels in the deeper layers of the dermis. The optical measurement of the reflectance of the tissue as the temperature is decreased represents the signal generated from different depths in the tissue. As described in U.S. Ser. No. 09/419,461, filed Oct. 15, 1999, depth of light penetration in tissue increases as temperature is lowered. Table I shows the mean light penetration depth in the skin of the forearm of seven light skinned non-diabetic volunteers, as summarized from the data in U.S. Ser. No. 09/419,461, filed Oct. 15, 1999. Because the change in light penetration depth as a function of temperature was found to differ between diabetic and non-diabetic volunteers, only the mean of the non-diabetic volunteers was included in Table 1.

As shown in Table 1, depth of penetration of light in tissue varies between 970 microns to 2020 microns, upon varying the wavelength from 590 nm to 950 nm, respectively. Depth of penetration of light in tissue further increases at each given wavelength as the temperature of the tissue varied from 38° C. to 22° C. The extent of change in light penetration depth upon reducing the temperature from 38° C. to 22° C. depends on the wavelength at which the measurement is performed. The percentage change in $\Delta\delta$ is higher at shorter wavelengths.

TABLE 1

| Wavelength of | Light penetration depth $\delta$ in skin in micrometers | | |
|---|---|---|---|
| Incident light⇒ | 590 nm | 750 nm | 950 nm |
| Temperature⇓ | | | |
| 38° C. | 970 ± 80 | 1800 ± 180 | 2020 ± 200 |
| 22° C. | 1110 ± 90 | 2060 ± 180 | 2210 ± 180 |
| Mean $\Delta\delta$ in microns | 130 | 260 | 190 |
| % change in $\Delta\delta$ | 14% | 14.4% | 9.9% |

Thus, it is possible to map an average depth in the tissue, i.e., from 970 micrometers to 2210 micrometers, by appropriate selection of a temperature between 22° C. and 38° C., and a wavelength of light between 590 nm and 950 nm. Increasing the temperature above 38° C. will lead to a shallower penetration of light into the tissue, and lowering the temperature below 22° C. will lead to deeper penetration of light into the tissue, e.g., the skin.

The method of this invention overcomes several difficulties that face methods of the prior art. One method of determination of blood glucose level involves determining the scattering coefficients of tissue. This method involves spatially resolved diffuse reflectance, wherein the intensity of light re-emitted from the sample is a function of the distance between the light introduction site and the light collection site measured on the surface of the sample. In this method, the intensity of the light re-emitted from the sample is analyzed mathematically to determine the values of the absorption coefficient and the scattering coefficient (see U.S. Pat. No. 5,551,422). Another method is the use of frequency domain measurements (see U.S. Pat. No. 5,492,118). Both methods depend on the variation in the scattering coefficient as a function of blood glucose level. The determination of the scattering coefficient is important for the spatially resolved diffuse reflectance method of U.S. Pat. Nos. 5,551, 422; 5,676,143; 5,492,118; and 5,057,695. The determination of the scattering coefficient is also important for the frequency domain method of U.S. Pat. Nos. 5,187,672; 5,122,974; 5,492,769 and 5,492,118.

The ability to accurately determine $\mu'_s$ and $\mu_a$ separately depends on the use of a diffusion theory approximation and requires a certain ratio of the scattering coefficient to the absorption coefficient ($\mu'_s>>\mu_a$). Accordingly, the wavelength range of the measurement must be limited to a range where this relationship holds. The diffusion theory approximation also requires a large sampling distance (separation between the light introduction site and the light collection site); hence, samples of tissue having large mass, such as skull, the biceps, or the calves are required for a reliable estimation of optical parameters. The diffusion theory approximation is also based on the assumption that human tissue is a homogeneous medium, which is contrary to what is known in the medical art. Several layers of the skin are histologically distinguishable, i.e., the epidermis (including the stratum corneum), the dermis, and cutaneous tissues. Each layer ranges from tens to hundreds of micrometers in thickness.

In a preferred embodiment of this invention, the distance between the light introduction site and the light collection site (or sites) is kept small (under 3 mm) to confine the volume observed of light interaction with tissue to approximately 1 mm³. The small sampling distance allows temperature to be controlled and modulated over a small volume of tissue. The use of a small sampling distance limits the use of the diffusion theory approximation to aid in calculating optical parameters of tissue.

EXAMPLES

The following non-limiting examples further illustrate the present invention.

Example 1

A temperature-controllable localized reflectance tissue photometer having the capability of controlling the temperature of the sample and varying the temperature of the sample within a small depth in the tissue was constructed. Details of the breadboard construction are described in WO 99/59464, incorporated herein by reference. As shown schematically in FIG. 1, the apparatus 10 comprises a light source module 12, an optical probe module 14, and a signal detection module 16. These three modules were interconnected through a branched optical fiber bundle.

The light source module comprised four light emitting diodes (LED's) 20, 22, 24, and 26, wherein the light output could be modulated. The LED's were mounted in a circular holder 28 and the light from the LED's was defocused and then focused on the end 30 of an illuminating element 32 by means of a 28 mm focal length RKE precision eyepiece 34 (Edmund Scientific part No 30787). Each LED was set to a different frequency. The wavelengths of the LED's and the frequency at which each one was set are shown in Table 2.

TABLE 2

| LED Number | Wavelength (nm) | Modulation frequency (Hz) | Half band width (nm) |
| --- | --- | --- | --- |
| 1 | 660 | 1024 | 15 |
| 2 | 590 | 819 | 15 |
| 3 | 935 | 585 | 25 |
| 4 | 890 | 455 | 25 |

A portion of the light was diverted by a beam splitter 36 and focused onto a silicon photodiode 38 (Model S-2386-44K 6C, Hamamatsu, Hamamatsu-city, Japan) and a pre-amplifier 40 to generate a reference signal, which was used to correct for fluctuations in intensity of the source of light. The remainder of the light beam was re-focused onto the end 30 of the illuminating element 32 housed at the source tip 42 of a 44.

An end 45 of the illuminating element 32 and the ends of the light collecting elements 46, 48, 50, and 52 were mounted in a common tip 54, situated at the center of a temperature-controlled disc 56 (2-cm diameter). The common tip 54 and the temperature-controlled disc 56 were parts of a body interface module 58. The body module 58 is in contact with the skin, designated herein by the letter "S." All of the elements 32, 46, 48, 50, and 52 were fibers made of low OH silica, and each had a diameter 400 µm (Fiberguide Industries, Stirling, N.J.). The distance from the center of each light collecting element 46, 48, 50, and 52 to the center of the illuminating element 32 defined the sampling distances $r_1$, $r_3$, $r_4$, and $r_6$ of this apparatus, which are set forth in Table 3.

The light re-emitted from the skin was collected by the light collecting elements 46, 48, 50, and 52 and transmitted to the signal detection module 16. A quadrant silicon photodiode detector 60 (Advanced Photonics, P/N SD225-2321-040) located in the detection module 16, measured the light intensity transmitted from the four light collecting elements 46, 48, 50, and 52. Only four were used in the measurement and were designated distances $r_1$, $r_3$, $r_4$, and $r_6$. The end of each light collecting element was located in a detection tip 62.

The optical probe of Example 1 was mounted on the left arm of a standard clinical reclining chair. The subject sat in the chair with the left arm resting in a cradle against the spring-loaded optical detection head, which was pressed against the dorsal side of the subject's forearm at a constant force of 160 grams (approximately 45 grams per cm²). A thermoelectric cooling/heating element 64 (Model SP1507-01AC, Marlow Industries, Dallas, Tex.) and a controller/power supply unit 66 (Marlow Industries, SE5000-02) controlled the temperature of the disc 56, which was placed in contact with the skin. A thermocouple 68 has the function of sensing the temperature in the aluminum disc 56 and providing a feedback to the temperature controller 66. A personal computer employing LabView™ (version 5.1, National Instruments, Austin, Tex.) software program controlled the temperature setting via the controller 66. The personal computer and its accompanying software also managed acquisition of data.

Light from the illuminating element 32 entered the skin through a body interface module 58 attached on the arm of the reclining clinical chair. The signals from four of the light collecting elements 46, 48, 50, and 52 were transmitted to the detector 60 (Advanced Photonics, P/N SD225-2321-040), one signal to each quadrant of the detector 60. The signal from each quadrant of the detector 60 was amplified separately and measured by means of a multimeter 70 (Hewlett-Packard, Palo Alto, Calif.). The optical signals were collected and integrated every 30 seconds, because of the limitations of the data transfer rate between the multimeter and the personal computer. The distances at which the signal was collected were $r_1$, $r_3$, $r_4$, and $r_6$ and set forth in Table 3.

TABLE 3

| Element | $r_1$ | $r_3$ | $r_4$ | $r_6$ |
| --- | --- | --- | --- | --- |
| Sampling distance in mm | 0.44 | 0.92 | 1.22 | 1.84 |

In general, sampling distances typically have a range of from about 0.2 mm to about 5 mm, preferably from about 0.2 mm to about 2 mm.

A calibration algorithm was used to correct for fluctuation in the intensity and spectral output of the LED's, spectral response of the detector, relative light throughput of the illuminating element and each light collecting element, and dark current of the detection system (i.e., the current of the detection system when the light source is turned off). Accordingly, the magnitude of the reflectance signal thus obtained differs from its true value only by a common multiplicative factor that is unique for each set of elements, detector, and type of lamp. For each sampling distance, r, and wavelength, λ, the reflectance parameter R'(r, λ) is defined as follows:

$$R'(r, \lambda) = \text{Log}_e(\text{Measured Localized Reflectance}) \tag{4}$$

The classical least square regression (CLSQ) method was used to establish calibration and validation models. Assuming that each concentration of each analyte modulates the optical parameters linearly, the concentration of analyte was expressed as a linear function of optical parameters, i.e., $$[Analyte] = a_0 + \sum_{i=1}^{n} a_i \cdot \text{Optical\_Parameter}_i \quad (5)$$

here, [Analyte] represents the concentration of the analyte, and Optical_Parameter$_i$ represents the $i^{th}$ optical parameter, in this case the reflectance at a defined distance, wavelength, and temperature. The coefficients $a_0$, $a_1$, $a_2$, . . . are determined from the egression. The Optical_Parameter$_i$ in this case was R'(r, λ) as defined by Equation (4).

Example 2

This example demonstrates the monitoring of changes in blood glucose level during a meal tolerance test (MTT) while the temperature of the skin is varied between two preset limits.

Three male volunteers (two diabetics, one non-diabetic) participated in several sessions of "meal tolerance tests" (MTT). Each MTT session lasted two hours. During the test sessions, each subject sat in a semi-reclining position and rested his left-forearm on the armrest. The optical probe was described in Example 1. For each subject, two test sessions were conducted during which the subject did not ingest any food or fluids. These were used as control runs. In one other control MTT session, the subject drank 300 mL of water. In the rest of the MTT sessions, the subject ingested a meal 15 minutes after the test had begun. The meals used were: a high sugar liquid (340 mL of cranberry-grape cocktail containing 59 g sugar), 11–34 g jellybeans, a doughnut, or an apple jelly sandwich. The meals increased the subject's blood sugar. The blood glucose level of each subject was monitored every 15 minutes by finger stick and tested with a home-use glucose meter (Bayer Elite®, Bayer Corporation, Elkhart, Ind.). In four additional tests, two of the subjects were given high protein, low-carbohydrates meals to induce the digestion process without significantly changing blood glucose levels. The reflectance of a piece of high scattering glass was measured to check the calibration of the optical probe described in Example 1 before and after each meal tolerance test session.

Figure 2A:
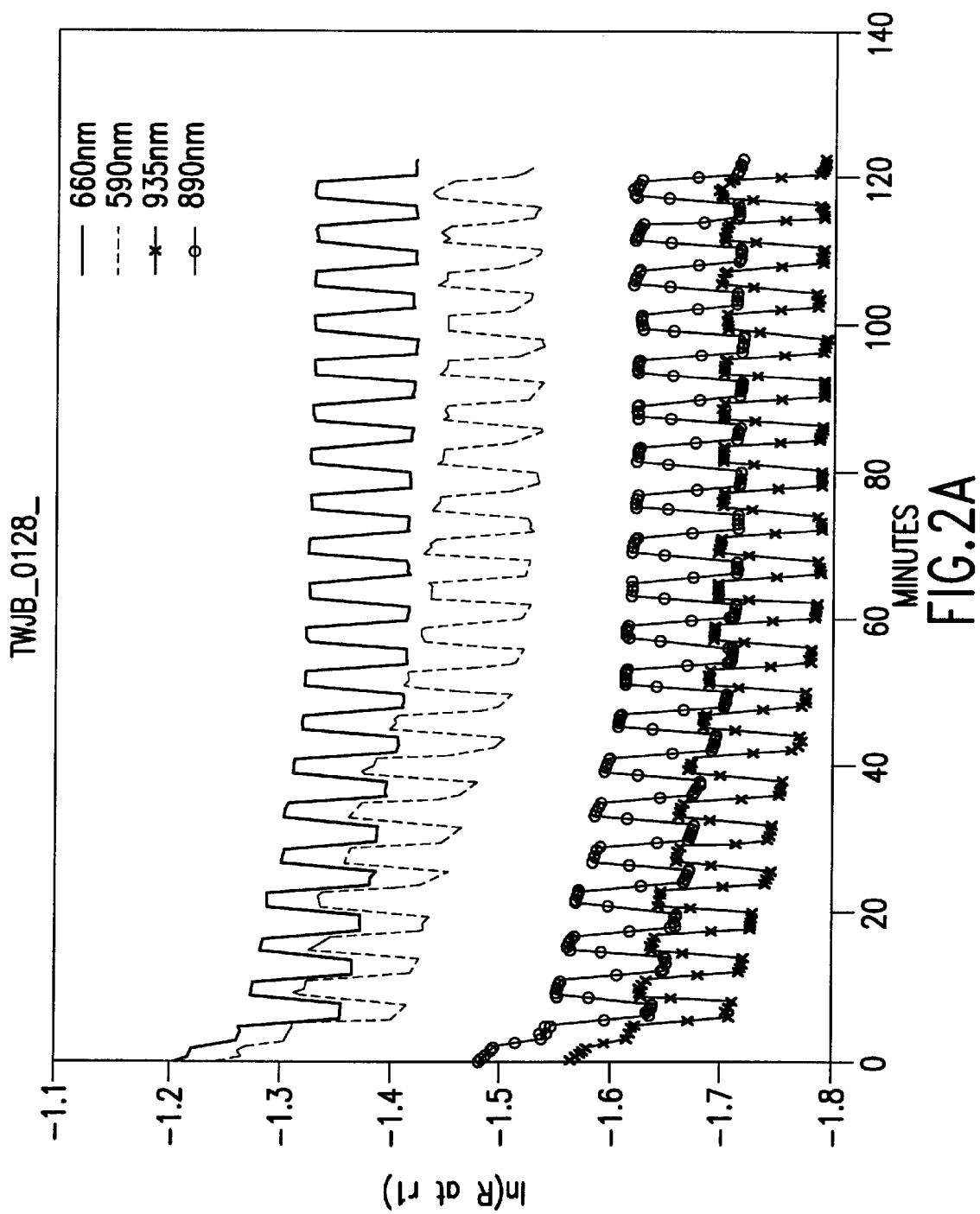
FIG. 2A is a graph illustrating the output signal during a meal tolerance test on a human subject as the temperature is being modulated between 22° C. and 38° C.
Figure 2B:
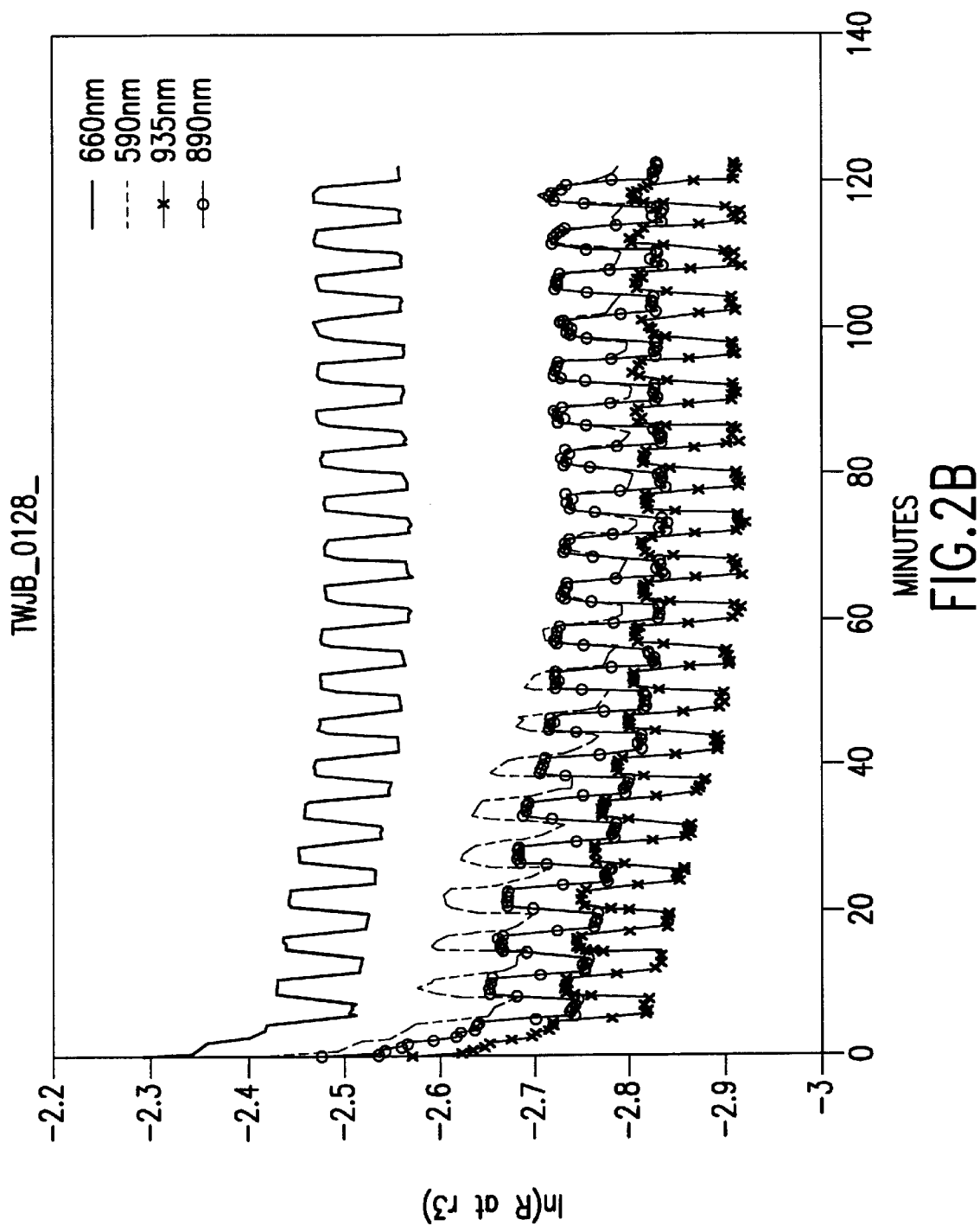
FIG. 2B is a graph illustrating the output signal during a meal tolerance test on a human subject as the temperature is being modulated between 22° C. and 38° C.
Figure 2C:
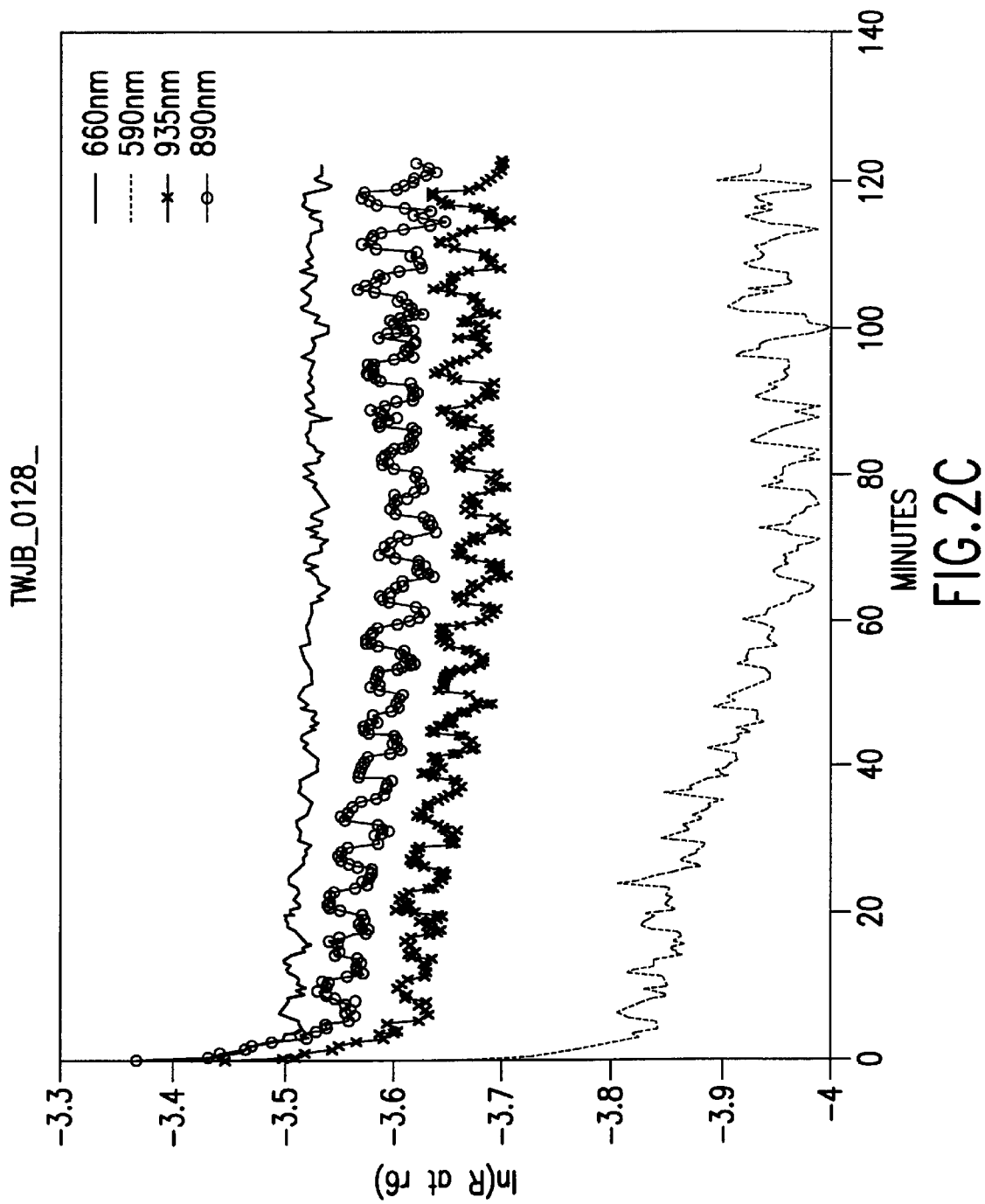
FIG. 2C is a graph illustrating the output signal during a meal tolerance test on a human subject as the temperature is being modulated between 22° C. and 38° C.

During a meal tolerance test, the temperature of the disc was repetitively modulated (cycled) between 38° C. and 22° C. at six minutes per cycle. Slightly more than one minute was required for the temperature to reach the targeted level when the disc was in contact with the human body. The temperature is preferably decreased or increased at a controlled rate during measurement of optical signals. Optical measurements (at four wavelengths and at four sampling distances) were taken every 30 seconds. Measurements at any given time, t, provided data at one of the four wavelengths and at one of the four sampling distances. The signals were converted to reflectance, R'(r, λ, t), by dividing the signal detected from the tissue by the signal generated from the scattering glass measurement taken before each meal tolerance test. FIGS. 2A, 2B, and 2C illustrates the results of these measurements.

The reflectance signals, measured at each of the four sampling distances and at each of the four wavelengths, were correlated over the two-hour period with changes in blood glucose levels. The reflectance data were expressed as the natural logarithm of R'(r, λ, t) at the end of every temperature segment. Two sequences of reflectance data corresponding to temperatures $T_1$ and $T_2$, were thus obtained. These were R'(at $T_1$)=Log$_e$R(r, λ, $T_1$) and R'(at $T_2$)=Log$_e$R(r, λ, $T_2$). For each MTT test over the two-hour period, the two temperature sequences encompassed 20 data points. Blood glucose levels were measured every 15 minutes by lancing a finger and performing a glucose determination by means of a Bayer Elite® home glucose monitor. The values of blood glucose level measured invasively were interpolated to generate values of blood glucose level at points in time in correspondence with optical measurements.

Table 4 summarizes the results of the four-term CLSQ regression using data generated at each of the preset fixed temperatures (either 22° C. or 38° C.), and the data of the four-term CLSQ regression when the temperature of the skin was varied between these two temperatures. The mathematical relationship between said optical parameter and said concentration of an analyte can derived by using at least one of several types of statistical methods, such as, for example, linear least squares, partial least squares, and principal component analysis.

Figure 3:
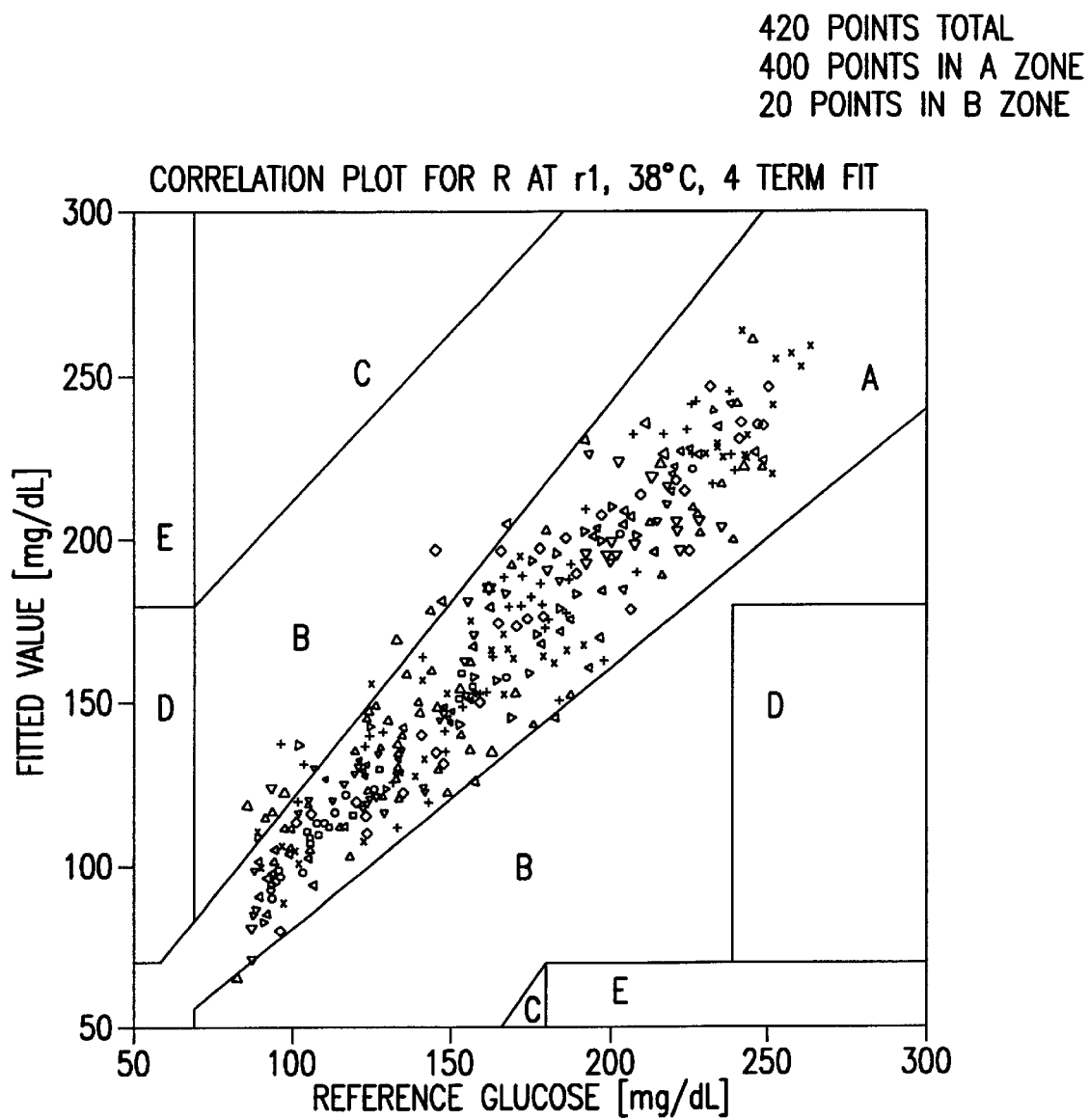
FIG. 3 is a graph illustrating a summary of the calibration data for three subjects. The presentation of data employs a Clarke Error Grid.

The data included meal tolerance tests for three subjects (two diabetics and one non-diabetic). The total number of data points was 420. These points were generated in 21 runs for the three subjects. The data are expressed as the calibration correlation coefficient and the standard error of calibration (SEC in mg/dL). Another way to present the quality of the data is the use of the Clarke Error Grid (W. Clarke, D. Cox, L. Gonder-Fredrick, W. Carter, and S. Pohl, "Evaluating clinical accuracy of systems for self-monitoring of blood glucose", *Diabetes Care* 1987; 10:622–628). The Clarke Error Grid is a scatter plot of the calculated blood glucose levels versus the reference blood glucose levels. The grid is divided into five zones, namely A, B, C, D, and E zones. Data points that are in the A and B zones are deemed acceptable, because they present values close to the reference blood glucose level or values that are not accurate but will not lead to wrong clinical intervention. Data points that are in the C, D, or E zones may lead to wrong clinical intervention and may jeopardize the health of the patient. The performance of the test device is considered to be better when the percentage of data points in the A zone increases and the percentage of data points in the B zone decreases. FIG. 3 illustrates data of this example by means of a Clarke Error Grid.

TABLE 4

| Sampling Distance (mm) | Temperature (° C.) | $r_c^2$ | SEC (mg/dL) | % data points in the A zone | % data points in the B zone |
|---|---|---|---|---|---|
| 1.84 | 22 | 0.88 | 16.3 | 91.19 | 8.81 |
| 1.22 | 22 | 0.86 | 16.6 | 91.67 | 8.33 |
| 0.92 | 22 | 0.90 | 14.5 | 95.48 | 4.52 |
| 0.44 | 22 | 0.90 | 14.3 | 94.52 | 5.48 |
| 1.84 | 38 | 0.88 | 15.3 | 92.62 | 7.38 |
| 1.22 | 38 | 0.88 | 15.1 | 92.86 | 7.14 |
| 0.92 | 38 | 0.90 | 14 | 94.52 | 5.48 |
| 0.44 | 38 | 0.90 | 14.2 | 95.24 | 4.76 |
| 1.84 | 38/22 | 0.94 | 11.9 | 96.43 | 3.57 |
| 1.22 | 38/22 | 0.92 | 12.6 | 95.95 | 4.05 |
| 0.92 | 38/22 | 0.94 | 10.6 | 97.38 | 2.62 |
| 0.44 | 38/22 | 0.94 | 11.3 | 96.86 | 2.14 |

Figure 4:
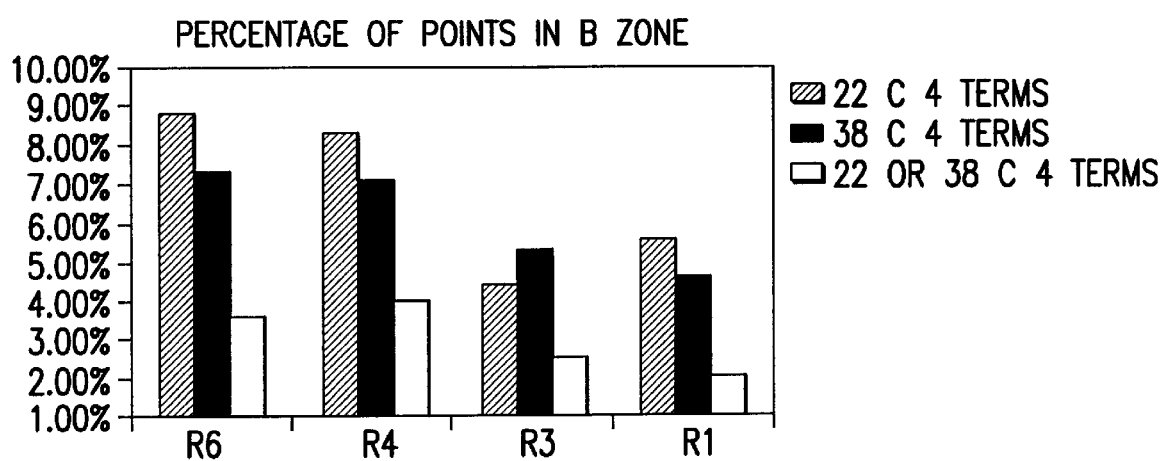
FIG. 4 is a graph illustrating a plot of the number of data points in the B zone of the Clarke Error Grid as the data points at one or two temperatures are used in the regression equation.

As shown in Table 4 and FIG. 4, at either of the temperatures and at the four sampling distances studied, the calibration correlation coefficient, expressed as $r_c^2$, was in the range between $r_c^2$=0.86 and $r_c^2$=0.90. The standard error of calibration (SEC) was in the range between 14.2 mg/dL and 16.6 mg/dL. More than 90% of the calibration data points were in the A zone of the Clarke Error Grid. The number of data points in the B zone of the Clarke Error Grid varied with the temperature and the sampling distance. At a single temperature, e.g. 22° C., the percentage of data points in the "B" zone varied between 8.81% for a sampling distance of 1.84 mm and 4.52% for a sampling distance of 0.92 mm. At the single temperature 38° C., the percentage of data points in the B zone varied between 7.38% for a sampling distance of 1.84 mm and 4.76% at a sampling distance of 0.44 mm. Thus, there was no substantial difference between the values of $r_c^2$, SEC, and percentage of the data points in the B zone when a single fixed temperature is used during the meal tolerance test, whether this temperature is above or below the body core temperature (37±1° C.). See FIG. 4.

The use of optical data obtained from measurements in which the temperature of the skin is modulated improved the calibration results. There was an increase in $r_c^2$ to a value greater than 0.92, a decrease in SEC to a value between 10.6 and 12.6 mg/dL, and a decrease in the percentage of data points in the B zone of the Clarke Error Grid. The percentage of data points in the A zone increased to exceed 95% and the percentage of data points in the B zone decreased to fall between 4.05% at a sampling distance of 1.22 mm and 2.14% at a sampling distance of 0.44 mm.

Thus, the calibration parameters for a spatially resolved diffuse reflectance measurement were improved when the temperature of the skin was cycled between pre-set limits and the optical data at the two temperatures were used in the CLSQ regression equation. It is important to note that all the calibration data presented in Table 6 were obtained at a single sampling distance. A plurality of light collection sites, a plurality of detectors, and a plurality of fibers were not required, thereby leading to simpler, more robust instruments that are easier to calibrate and maintain. Further, the method of this invention does not rely on calculating optical parameters that depend on the diffusion theory approximation or Monte Carlo simulations. Thus the calibration parameters obtained are independent of the assumptions that are usually used when applying the diffusion theory approximation or the Monte Carlo simulations.

Example 3

The results of the meal tolerance test experiments of Example 2 were analyzed to determine the terms that contributed to the model at a single sampling distance. The results were further analyzed to determine the ability of each of these models to predict glucose concentration non-invasively in other experiments. Calibration models based on a single day's meal tolerance test results were established and used to predict the blood glucose level during meal tolerance tests or control tests conducted on other days.

In order to analyze the data, multivariate models were restricted to four optical parameters to avoid overfitting. Calibration data was obtained at a single sampling distance of 0.92 mm. Calibration data at the sampling distance of 0.92 mm for a diabetic subject are shown in Table 5. Each run, i.e., meal tolerance test, was identified by the initials of the subject and a number, which number indicated the day in the experimental sequence that the meal tolerance test was run or control run was performed. The 4-term CLSQ regression equations at the distance of 0.92 mm and the two preset temperature limits between which the temperature of the surface of the skin was modulated employed four terms—each term employed a different combination of temperature and wavelength. The calibration correlation coefficient $r_c$ and the standard error of calibration SEC, expressed in mg/dL of glucose, are also shown in Table 5.

TABLE 5

| Test | CLSQ regression 4-term fitting equation at a sampling distance of 0.92 mm | $r_c$ | SEC (mg/dL) |
|---|---|---|---|
| STW1 control | [G] = [5.65 − 1.32 R'(660 nm/22° C.) + 0.278 R'(590 nm/22° C.) + 5.15 R'(935 nm/38° C.) − 1.77 R'(890 nm/38° C.)] × 1000 | 0.95 | 9.22 |
| STW2 control | [G] = [−9.61 + 2.10 R'(660 nm/22° C.) − 1.03 R'(590 nm/22° C.) − 7.71 R'(935 nm/38° C.) + 2.30 R'(890 nm/38° C.)] × 1000 | 0.96 | 13.2 |
| STW3 meal | [G] = [−4.25 + 2.49 R'(660 nm/22° C.) − 4.73 R'(590 nm/22° C.) − 9.42 R'(935 nm/38° C.) − 3.07 R'(890 nm/38° C.)] × 1000 | 0.93 | 14.9 |
| STW4 meal | [G] = [−2.72 − 2.16 R'(660 nm/22° C.) − 2.51 R'(590 nm/22° C.) − 2.99 R'(935 nm/38° C.) − 7.96 R'(890 nm/38° C.)] × 1000 | 0.95 | 11.3 |
| STW7 meal | [G] = [−3.12 + 4.82 R'(660 nm/22° C.) − 8.30 R'(590 nm/22° C.) + 2.48 R'(935 nm/38° C.) − 5.43 R'(890 nm/38° C.)] × 100 | 0.94 | 16.9 |
| STW8 meal | [G] = [−4.01 − 3.79 R'(660 nm/22° C.) − 1.76 R'(590 nm/22° C.) + 9.10 R'(935 nm/38° C.) − 1.08 R'(890 nm/38° C.)] × 1000 | 0.92 | 10.1 |
| STW9 meal | [G] = [−5.60 − 3.10 R'(660 nm/22° C.) − 1.83 R'(590 nm/22° C.) − 1.52 R'(935 nm/38° C.) + 1.80 R'(890 nm/38° C.)] × 1000 | 0.94 | 15.7 |

The data ($r_c$ and SEC) in Table 5 show the ability of the method of this invention to successfully establish a model that correlates blood glucose level with reflectance signal. This particular model employed reflectance signals at a sampling distance of 0.92 mm at four wavelengths, as the temperature was modulated between two set temperatures (22° C. and 38° C.). The calibration correlation coefficient ranged from 0.92 to 0.96, and the standard error of calibration ranged from 9.2 mg/dL to 16.9 mg/dL. Similar data were obtained at sampling distances of 0.44 mm and 1.84 mm. Also, similar correlation coefficient and SEC results were obtained for the other two subjects.

The CLSQ regression models shown in Table 5 reveal a significant pattern. The light of the short wavelengths, under 800 nm, e.g., 590 nm and 660 nm, is paired with the low temperature 22° C.; the light of the long wavelengths, over 800 nm, e.g., 890 nm and 935 nm, is paired with the higher temperature 38° C. As shown in Table 1 and described in U.S. Ser. No. 09/419,461, filed Oct. 15, 1999, the depth of penetration of light in tissue at 38° C. is shallower than is the depth of penetration of light in tissue at 22° C. The depth of penetration of light at the shorter wavelengths is shallower than is the depth of penetration of light at the longer wavelengths. The CLSQ regression models in Table 5 indicate that the interaction between light and tissue that was accounted for by this model occurs in a specified cutaneous region of the skin. This region is located at a depth confined between the depth specified by the penetration expected at shorter wavelengths and lower temperatures and the depth specified by the penetration expected at longer wavelengths and higher temperatures. In effect, the selection of a temperature and a wavelength specifies a cutaneous volume in the skin that provides a satisfactory calibration correlation between the optical signal detected and the blood glucose level. The data also indicate that a calibration relationship between the reflectance signal at a single sampling distance and blood glucose level can be generated without performing a spatially resolved diffuse reflectance measurement of the scattering coefficient as described in U.S. Pat. Nos. 5,551,422; 5,676,143; 5,492,118; and 5,057,695.

The use of the derived CLSQ regression models to predict the concentration of glucose in capillary blood is shown in Tables 6A, 6B, and 6C. Table 6A shows the standard error of prediction (SEP) for non-invasive glucose determinations using the models in Table 5 for subject STW. Table 6B shows the standard error of prediction (SEP) for non-invasive glucose determinations using a model similar to that in Table 5 for subject HTM. Table 6C shows the standard error of prediction (SEP) for non-invasive glucose determinations using a model similar to that in Table 5 for subject TWJ. The SEP is expressed in mg/dL. The CLSQ model for each day (listed in the first column) was used to predict the blood glucose level for other days in the experimental sequence. Thus, in the row designated STW1, the calibration model generated on the first day was used to predict the blood glucose level in the other days in the experimental sequence (days 2 through 9). Similarly, in the row designated STW2, the calibration model generated on the second day was used to predict the blood glucose level in the other days in the experimental sequence (day 1, and days 3 through 9). The values in the top row indicate the range of change of blood glucose level between the lowest and highest value during the meal tolerance test (expressed in mg/dL). The underlined values indicate the standard error of prediction values (SEP) that were deemed acceptable for all three subjects by the criterion that the standard error of prediction (SEP) is equal to or less than 36 mg/dL.

TABLE 6A

Standard error of prediction of glucose for subject STW

| | | Predict: | | | | | | | | |
|---|---|---|---|---|---|---|---|---|---|---|
| model | [G] range | STW1 control 100.8 | STW2 control 124.7 | STW3 meal 120 | STW4 meal 115.7 | STW5 control 21.4 | STW6 control 35.4 | STW7 meal 126.8 | STW8 meal 80.1 | STW9 meal 129.9 |
| STW1 control | 100.8 | 9.2 | 64.0 | 74.8 | 73.3 | 26.7 | 23.1 | 101.0 | 76.7 | 110.1 |
| STW2 meal | 124.7 | 89.0 | 13.2 | 39.1 | 51.0 | 53.1 | 65.7 | 75.2 | 82.8 | 97.7 |
| STW3 meal | 120 | 57.9 | 23.4 | 14.9 | 15.9 | 36.7 | 46.3 | 26.7 | 46.8 | 41.6 |
| STW4 meal | 115.7 | 48.2 | 30.1 | 21.5 | 11.3 | 24.5 | 29.7 | 30.7 | 18.4 | 31.0 |
| STW7 meal | 126.8 | 50.9 | 33.4 | 27.8 | 27.0 | 46.5 | 41.9 | 16.9 | 48.4 | 26.9 |
| STW8 meal | 80.1 | 63.5 | 34.5 | 50.1 | 44.8 | 60.2 | 31.0 | 51.6 | 10.1 | 47.5 |
| STW9 | 129.9 | 71.7 | 46.5 | 44.3 | 24.0 | 29.2 | 25.4 | 38.7 | 44.2 | 15.7 |

TABLE 6B

Standard error of prediction of glucose for subject HTM

| | | Predict | | | | | | | | |
|---|---|---|---|---|---|---|---|---|---|---|
| model | [Gp] range | HTM1 control 3.4 | HTM2 meal 85.1 | HTM3 meal 83.6 | HTM4 meal 114.9 | HTM5 control 0 | HTM6 control 16.3 | HTM7 meal 15.3 | HTM8 meal 66.4 | HTM9 meal 62.6 |
| HTM2 meal | 85.1 | 49.0 | 8.8 | 67.2 | 54.8 | 111.2 | 35.3 | 50.1 | 35.4 | 77.5 |
| HTM3 meal | 83.6 | 16.4 | 28.4 | 23.3 | 36.9 | 38.3 | 21.9 | 32.6 | 53.1 | 21.5 |
| HTM4 meal | 114.9 | 22.4 | 23.2 | 35.6 | 29.2 | 48.8 | 21.5 | 18.1 | 25.7 | 36.0 |
| HTM8 meal | 66.4 | 26.7 | 17.0 | 41.1 | 39.3 | 48.3 | 18.1 | 33.1 | 14.9 | 44.3 |
| HTM9 meal | 62.6 | 10.0 | 30.1 | 29.2 | 39.6 | 28.4 | 14.0 | 10.6 | 38.9 | 10.1 |

TABLE 6C

Standard error of prediction of glucose for subject TWJ

| | | Predict | | | | | | | | | |
|---|---|---|---|---|---|---|---|---|---|---|---|
| model | [G] range | TWJ1 control 12.6 | TWJ2 meal 69.2 | TWJ3 meal 65.1 | TWJ4 meal 62.9 | TWJ5 control 54 | TWJ6 control 54.8 | TWJ7 meal 130.9 | TWJ8 meal 116.3 | TWJ9 meal 123.2 | TWJ10 meal 126.5 |
| TWJ2 meat | 69.2 | 10.0 | 10.7 | 8.8 | 49.1 | 54.6 | 27.5 | 25.4 | 32.5 | 26.0 | 17.4 |
| TWJ3 meal | 65.1 | 6.0 | 20.6 | 7.3 | 78.7 | 84.3 | 15.9 | 26.3 | 33.0 | 28.4 | 19.4 |

TABLE 6C-continued

Standard error of prediction of glucose for subject TWJ

| model | [G] range | Predict TWJ1 control 12.6 | TWJ2 meal 69.2 | TWJ3 meal 65.1 | TWJ4 meal 62.9 | TWJ5 control 54 | TWJ6 control 54.8 | TWJ7 meal 130.9 | TWJ8 meal 116.3 | TWJ9 meal 123.2 | TWJ10 meal 126.5 |
|---|---|---|---|---|---|---|---|---|---|---|---|
| TWJ4 meal | 62.9 | 11.2 | 24.1 | 15.4 | 8.1 | 17.0 | 35.2 | 36.4 | 39.9 | 52.4 | 47.8 |
| TWJ5 control | 54 | 4.6 | 38.9 | 29.5 | 19.0 | 1.7 | 10.4 | 68.7 | 52.8 | 56.3 | 59.0 |
| TWJ6 control | 54.8 | 5.6 | 16.2 | 18.7 | 50.9 | 57.6 | 4.5 | 49.5 | 45.9 | 28.8 | 24.8 |
| TWJ7 meat | 130.9 | 22.6 | 13.7 | 19.3 | 21.6 | 32.5 | 59.5 | 13.0 | 25.9 | 37.3 | 34.9 |
| TWJ8 meal | 116.3 | 35.8 | 35.0 | 48.7 | 31.3 | 21.7 | 78.4 | 22.8 | 10.4 | 26.8 | 22.6 |
| TWJ9 meat | 123.2 | 30.0 | 25.9 | 32.7 | 48.5 | 43.7 | 64.5 | 20.8 | 13.7 | 18.6 | 20.4 |
| TWJ10 meal | 126.5 | 10.2 | 17.0 | 11.7 | 52.8 | 59.1 | 28.7 | 23.4 | 29.1 | 20.8 | 13.4 |

For subject STW, the calibration model of day 2 does not predict the glucose concentration for days 1 and 3–9. Other physiological or experimental conditions combined with the nature of the subject's skin produced this effect. Ignoring the results of day 2 as a calibration model for predicting glucose level led to a prediction success rate of 51.8% for subject STW.

The underlined values in the table designate successful predictions of the blood glucose level. The rate of successful predictions was calculated to be 44.4% for subject STW, based on the above-mentioned criteria. The other two subjects had similar results, with one diabetic subject (subject TWJ) having a prediction success rate of 71.1% and the non-diabetic subject (subject HTM) having a prediction success rate of 62.2%. These results compare well with data in the literature, where the ability to predict values of blood glucose level was found in only one out of five subjects. See Burmeister et al., Diabetes Therapeutics and Technology, Vol. 2, pages 5–16 (2000), where the glucose concentration could be predicted successfully in only one out of five subjects.

Thus, it was possible develop a calibration relationship between the optical signal measured at a single sampling distance and the blood glucose level by using reflectance data obtained at four wavelengths and two temperatures. It was also possible predict blood glucose level by means of the optical signal measured at a single sampling distance and calibration models based on reflectance data obtained at the same sampling distance and at a plurality of wavelengths and temperatures. It is important to note that all the calibration data presented in Tables 4 and 5 were obtained at a single sampling distance, without the need to perform spatially resolved diffuse reflectance measurements, or to determine the scattering coefficient. Avoiding the use of spatially resolved diffuse reflectance measurement and frequency domain measurement eliminates the need for having a plurality of light collection sites and for using a plurality of detectors or a plurality of optical fibers. This invention allows the use of simpler, more robust instruments that are easy to calibrate and to maintain. Further, the method of this invention does not rely on calculating optical parameters that depend on a diffusion theory approximation or on Monte Carlo simulations. Thus, the calibration parameters obtained are independent of the assumptions that are typically used when applying a diffusion theory approximation or a Monte Carlo simulation.

The method of this invention can also be used to determine the concentration of other analytes, such as, for example, urea, triglycerides, hemoglobin, and hematocrit.

Various modifications and alterations of this invention will become apparent to those skilled in the art without departing from the scope and spirit of this invention, and it should be understood that this invention is not to be unduly limited to the illustrative embodiments set forth herein.

What is claimed is:

1. A method for establishing a calibration relationship to determine the concentration of an analyte or a disease state in a biological tissue, said method comprising the steps of:
   (a) selecting a sampling area on the surface of said biological tissue;
   (b) setting the temperature of said sampling area of said biological tissue to a first temperature;
   (c) introducing light at a light introduction site, said light introduction site being within said sampling area and collecting light re-emitted at a light collection site, said light collection site being within said sampling area, said light introduction site and said light collection site being separated by a sampling distance, said introduced light being within a first wavelength range;
   (d) performing at least one optical measurement at said sampling distance;
   (e) setting the temperature of said sampling area of said biological tissue to a second temperature, said second temperature being different from said first temperature;
   (f) repeating steps (c) and (d) at said second temperature, said introduced light at said second temperature being within a second wavelength range;
   (g) determining the value of at least one optical parameter at said first temperature and at at least one wavelength within said first wavelength range and the value of said at least one parameter at said second temperature and at at least one wavelength within said second wavelength range; and
   (h) establishing a mathematical relationship that relates the value of said at least one optical parameter at said first temperature and at said at least one wavelength within said first wavelength range and the value of said at least one optical parameter at said second temperature and at said at least one wavelength within said second wavelength range with an independently measured concentration of said analyte or an independent measurement of said disease state.

2. The method of claim 1, wherein said temperatures at which said sampling area of said tissue is set are from about 10° C. to about 45° C.

3. The method of claim 1, wherein said temperatures at which said sampling area of said tissue is set are from about 15° C. to about 42° C.

4. The method of claim 1, wherein said temperatures at which said sampling area of said tissue is set are from about 20° C. to about 40° C.

5. The method of claim 1, wherein said light introduced to said tissue has at least one wavelength of from about 400 nm to about 2000 nm.

6. The method of claim 1, wherein said light introduced to said tissue has at least one wavelength of from about 500 nm to about 1800 nm.

7. The method of claim 1, wherein said light introduced to said tissue has at least four wavelengths, at least two of said wavelengths being from about 500 nm to about 800 nm, and at least two of said wavelengths being from about 800 nm to about 1100 nm.

8. The method of claim 1, wherein said sampling distance is from about 0.2 mm to about 5 mm.

9. The method of claim 1, wherein said sampling distance is from about 0.2 mm to about 2 mm.

10. The method of claim 1, wherein said temperature is repetitively modulated between two levels of temperature during measurement of an optical signal.

11. The method of claim 1, wherein said temperature is decreased at a controlled rate during measurement of an optical signal.

12. The method of claim 1, wherein said temperature is increased at a controlled rate during measurement of an optical signal.

13. The method of claim 1, wherein said analyte is selected from the group consisting of glucose, urea, triglycerides, hemoglobin, and hematocrit.

14. The method of claim 1, wherein said mathematical relationship between said optical parameter and said concentration of said analyte is derived by using a method selected from the group of statistical methods consisting of linear least squares, partial least squares, and principal component analysis.

15. A method for determining the concentration of an analyte or a disease state in a biological tissue, said method comprising the steps of:

(a) defining a sampling area on the surface of said biological tissue;

(b) setting the temperature of said sampling area of said biological tissue to a first temperature;

(c) introducing light at a light introduction site, said light introduction site being within said sampling area and collecting light re-emitted at a light collection site, said light collection site being within said sampling area, said light introduction site and said light collection site being separated by a sampling distance, said introduced light being within a first wavelength range;

(d) performing at least one optical measurement at said sampling distance;

(e) setting the temperature of said sampling area of said biological tissue to a second temperature, said second temperature being different from said first temperature;

(f) repeating steps (c) and (d) at said second temperature, said introduced light at said second temperature being within a second wavelength range;

(g) determining the value of at least one optical parameter at said first temperature and at at least one wavelength in said first wavelength range and the value of said at least one optical parameter at said second temperature and at at least one wavelength in said second wavelength range;

(h) establishing a mathematical relationship that relates the value of said at least one optical parameter at said first temperature and at said at least one wavelength within said first wavelength range and the value of said optical parameter at said second temperature and at said at least one wavelength within said second wavelength range with an independently measured concentration of analyte or an independent measurement of said disease state; and (i) determining the concentration of said analyte or said disease state by subsequent optical measurements of the value of said optical parameter at said first temperature and at at least one wavelength within said first wavelength range and the value of said optical parameter at said second temperature and at at least one wavelength within said second wavelength range.

16. The method of claim 15, wherein said temperatures at which said sampling area of said tissue is set are from about 10 ° C. to about 45° C.

17. The method of claim 15, wherein said temperatures at which said sampling area of said tissue is set are from about 15 ° ° to about 42° C.

18. The method of claim 15, wherein said temperatures at which said sampling area of said tissue is set are from about 20° C. to about 40° C.

19. The method of claim 15, wherein said light introduced to said tissue has at least one wavelength of from about 400 nm to about 2000 nm.

20. The method of claim 15, wherein said light introduced to said tissue has a wavelength of from about 500 nm to about 1800 nm.

21. The method of claim 15, wherein said light introduced to said tissue has at least four wavelengths, at least two of said wavelengths being from about 500 nm to about 800 nm, and at least two of said wavelengths being from about 800 nm to about 1100 nm.

22. The method of claim 15, wherein said sampling distance is from about 0.2 mm to about 5 mm.

23. The method of claim 15, wherein said sampling distance is from about 0.2 mm to about 2 mm.

24. The method of claim 15, wherein said temperature is repetitively modulated between two levels of temperature during measurement of an optical signal.

25. The method of claim 15, wherein said temperature is decreased at a controlled rate during measurement of an optical signal.

26. The method of claim 15, wherein said temperature is increased at a controlled rate during measurement of an optical signal.

27. The method of claim 15, wherein said analyte is selected from the group consisting of glucose, urea, triglycerides, hemoglobin, and hematocrit.

* * * * *

UNITED STATES PATENT AND TRADEMARK OFFICE
CERTIFICATE OF CORRECTION

PATENT NO.     : 6,526,298 B1
DATED          : February 25, 2003
INVENTOR(S)    : Omar S. Khalil et al.

It is certified that error appears in the above-identified patent and that said Letters Patent is hereby corrected as shown below:

Column 23,
Line 8, replace "10ºC." with -- 10ºC --.
Line 11, replace "15ºC." with -- 15ºC --.
Line 14, replace "20ºC." with -- 20ºC --.

Column 24,
Line 30, replace "10ºC." with -- 10ºC --.
Line 33, replace "15º º" with -- 15ºC --.
Line 36, replace "20ºC." with -- 20ºC --.

Signed and Sealed this

Sixth Day of July, 2004

JON W. DUDAS
*Acting Director of the United States Patent and Trademark Office*